Figure 1:
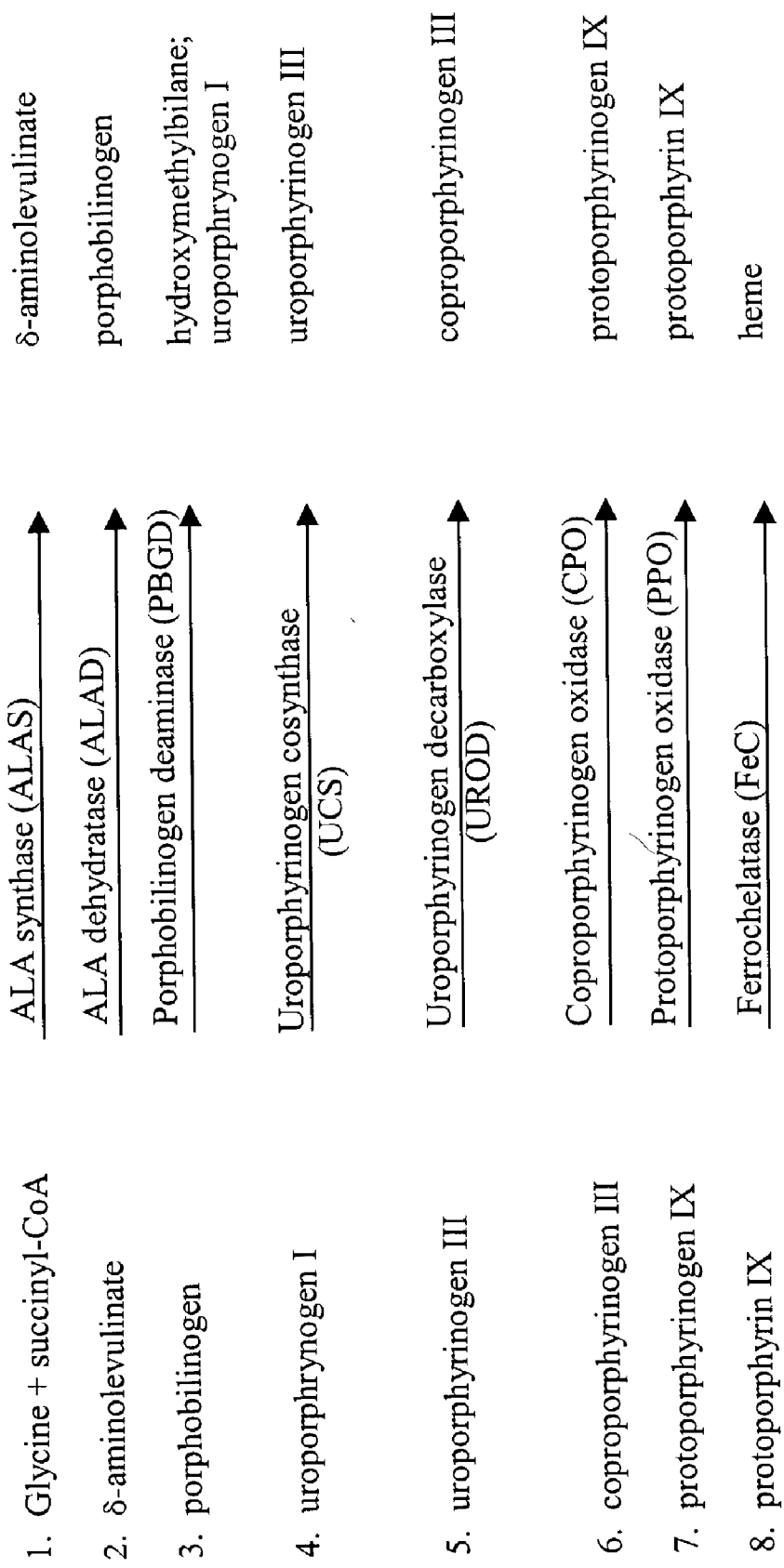

US007261887B2

(12) United States Patent
Chang et al.

(10) Patent No.: US 7,261,887 B2
(45) Date of Patent: Aug. 28, 2007

(54) ***LEISHMANIA* AS CARRIERS FOR THE DELIVERY OF PROTEINS AND PEPTIDES**

(75) Inventors: Kwang-Poo Chang, Kenilworth, IL (US); Shigeru Sassa, Tokyo (JP); Jerome F. Sah, Shaker Heights, OH (US); Hiroya Ito, Kagoshima (JP); Bala Krishna Kolli, Waukegan, IL (US); Daniel A. Peterson, Lake Villa, IL (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 6 days.

(21) Appl. No.: 10/293,867

(22) Filed: Nov. 12, 2002

(65) Prior Publication Data

US 2004/0092467 A1 May 13, 2004

(51) Int. Cl.
*A61K 48/00* (2006.01)
*C12N 1/11* (2006.01)

(52) U.S. Cl. ................. 424/93.21; 424/93.1; 424/93.2; 435/258.3; 435/471

(58) Field of Classification Search ................ 430/325, 430/455; 424/93.2, 93.21; 435/325, 455
See application file for complete search history.

(56) References Cited

FOREIGN PATENT DOCUMENTS

| | | |
|---|---|---|
| WO | WO98/11245 | 3/1998 |
| WO | WO 01/32896 | 5/2001 |
| WO | WO 02/44355 | 6/2002 |

OTHER PUBLICATIONS

Hughes et al., "Phylogeny of Trypanosomatidiae and Bodonidae (Kinetoplastida) based on 18S rRNA: evidence for paraphyly of Trypanosoma and six other genera," Mol. Biol. Evol. 20(4): 644-652, Apr. 2003.*

Vaccaro, D.E., "Symbiosis therapy: the potential of using human protozoa for molecular therapy," Mol. Ther. 2(6): 535-538, Dec. 2000.*

Wang et al., "Genetic Control of Chlorophyll Biosynthesis in Chlamydomonas: Analysis of a Mutant Affecting Synthesis of δ-Aminolevulinic Acid", *Cell*, vol. 76, 75-84, Sep. 1975.

LeBowitz et al., "Development of a Stable *Leishmania* Expression Vector and Application to the Study of Parasite Surface Antigen Genes", *Proc. Natl Acad. Sci. USA*, vol. 87, pp. 9736-9740,Dec. 1990.

Kurlandzka et al., The Alternative Pathway of Haem Synthesis via Dehydroisocoproporphyrinofen in Mutants of *Saccharomyces cerevisiae* Partially Deficient in Uroporphyrinogen Decarboxylase Activity, *J.B. Letters*, vol. 273, pp. 246-247, 1990.

Afonso et al., "Photodynamic and Non-Photodynamic Action of Several Porphyrins on the Activity of Some Heme-Enzymes", *J. Enzyme Inhibition*, 1990, vol. 3, pp. 303-310.

LeBowitz et al., "Thymidine Kinase as a Negative Selectable Marker in *Leishmania major*", *Molecular and Biochemical Parasitology*, vol. 51 (1992), pp. 321-326.

Spikes et al., "Photosensitizing Properties of Mono-L-Aspartyl Chlorin $e_6$ (NPe6): A Candidate Sensitizer for the Photodynamic Therapy of Tumors", *J. Photochem. Photobiol. B: Biol.*, vol. 17 (1993), pp. 135-143.

Kaye et al., "Antigens Targeted to the *Leishmania* Phagolysosome Are Processed for CD4+ T Cell Recognition", *Eur. J. Immunol.*, 1993, vol. 23, pp. 2311-2319.

Du et al., "Monophyletic Origin of β-division Proteobacterial Endosymbionts and Their Coevolution with Insert Trypanosomatid Protozoa *Blastocrithidia culicis* and *Crithidia* spp.", *Proc. Natl Acad. Sci. USA*, vol. 99, pp. 8437-8441, Aug. 1994.

Titus et al., "Development of a Safe Live *Leishmania* Vaccine Line by Gene Replacement", *Proc. Natl. Acad. Sci. USA*, vol. 99, pp. 10267-10271, Oct. 1995.

Sassa et al., "The Role of Heme in Gene Expression", *International Journal of Hematology*, vol. 63 (1996), pp. 167-178.

Castro et al., "The Concept of Laser Phototherapy", *Otolaryngologic Clinics of North America*, vol. 29, No. 6, Dec. 1996, pp. 1011-1029.

Chakrabarty et al., "Kinetics of Entry of Virulent and Avirulent Strains of *Leishmania donovani* into Macrophages: A Possible Role of Virulence Molecules (gp63 an LPG)", *J. Parasitol*, vol. 82(4), 1996, pp. 632-635.

Peng et al., "5-Aminolevulinic Acid-Based Photodynamic Therapy", *Cancer*, Jun. 15, 1997, vol. 79, No. 12, pp. 2282-2308.

Abels et al., "Photodynamic Therapy with 5-Aminolaevulinic Acid-Induced Porphyrins of an Amelanotic Melanoma In Vivo", *Journal of Photochemistry and Photobiology B: Biology*, vol. 40 (1997), pp. 76-83.

M. Wainright, "Photodynamic Antimicrobial Chemotherapy (PACT)", *Journal of Antimicrobial Chemotherapy*, 1998, vol. 42, pp. 13-28.

Alexander et al., "*Leishmania mexicana* Cysteine Proteinase-Deficient Mutants Have Attenuated Virulence for Mice and Potentiate a Th1 Response", *Journal of Immunology*, 1998, vol. 161, pp. 6794-6801.

Gibson et al., "δ-Aminolaevulinic Acid-Induced Photodynamic Therapy Inhibits Protoporphyrin IX Biosynthesis and Reduces Subsequent Treatment Efficacy In Vitro", *British Journal of Cancer*, (1999) vol. 80(7), pp. 998-1004.

Chang et al., "*Leishmania* Virulence and Genetic Heterogeneity", *Clinics in Dermatology*, 1999, vol. 17, pp. 269-273.

S.Sassa, "Hematologic Aspects of the Porphyrias", *International Journal of Hematology*, 2000, vol. 17, pp. 1-17.

(Continued)

*Primary Examiner*—Scott D. Priebe
(74) *Attorney, Agent, or Firm*—Everest Intellectual Property Law Group; Tin-Chuen Yeung

(57) ABSTRACT

Methods for delivering potentially therapeutic or prophylactic protein and peptide agents to mammalian cells are provided. The agents are delivered by mutant trypanosomatid protozoa that have been genetically manipulated to code for such protein or peptide agents. The mutant protozoa additionally lack certain enzymes within the heme biosynthetic pathway, making the mutants susceptible to porphyria and eventual lysis.

15 Claims, 8 Drawing Sheets
(2 of 8 Drawing Sheet(s) Filed in Color)

OTHER PUBLICATIONS

Mollenkopf et al., "Intracellular Bacteria as Targets and Carriers for Vaccination", *Biological Chemistry*, vol. 382, Issue 4 (Apr. 2001), pp. 521-532.

Gourley et al., "Pteridine Reductase Mechanism Correlates Pterin Metabolism with Drug Resistance in Trypanosomatid Parasites", *Nature Structural Biology*, vol. 8, No. 6, Jun. 2001, pp. 521-525.

Taylor et al., "The Advantages of Aminolevulinic Acid Photodynamic Therapy in Dermatology", *Journal of dermatological Treatment*, vol. 13, Suppl. 1 (2002), pp. S3-S11.

Friesen et al., "5-Aminolevulinic Acid-Based Photodynamic Detection and Therapy of Brain Tumors", *International Journal of Oncology*, vol. 21, 2002, pp. 577-582.

Edgeworth et al., "Vaccine Development Against HIV-1", *Immunologic Research*, vol. 25, No. 1 (2002), pp. 53-74.

Papadopoulou et al., "Reduced Infectivity of a *Leishmania donovani* Biopterin Transporter Genetic Mutant and Its Use as an Attenuated Strain for Vaccination", *Infection and Immunity*, vol. 70, No. 1, Jan. 2002, pp. 62-68.

Sah et al., "Genetic Rescue of *Leishmania* Deficiency in Porphyrin Biosynthesis Creates Mutants Suitable for Analysis of Cellular Events in Uroporphyria and for Photodynamic Therapy", *Journal of Biological Chemistry*, vol. 277, No. 17, Apr. 26, 2002, pp. 14902-14909.

Tetaud et al., "A New Express Vector for *Crithidia fasciculata* and *Leishmania*", *Molecular and Biochemical Parasitology*, vol. 120 (2002), pp. 195-204.

Bissonnette et al., "Systemic Photodynamic Therapy with Aminolevulinic Acid Induces Apoptosis in Lesional T Lymphocytes of Psoriatic Plaques", *Journal of Investigative Dermatology*, vol. 119, No. 1, Jul. 2002, pp. 77-83.

Breitling et al., Non-pathogenic trypanosomatid protozoa as a platform for protein research and production, *Protein Expression and Purification* 25 (2002) 209-218.

S. Adler, "The Behaviour of a Lizard *Leishmania* in Hamsters and Baby Mice", Rev. Inst. Med. Trop. Sao Paolo, 4:61-64, 1962.

Olobo et al., "Uptake of Promastigotes of a Lizard *Leishmania* sp. and *Leishmania denovani* By Mouse Peritoneal Macrophages". Acta Tropica 40, 89-91 (1983).

Rozenthal et al., "Influences of the Endosymbiont on the Interaction of *Crithidia denal* wtih Microphages", Microce Electron Biol Celular. Dec. 1987; 11(2), pp. 167-176.

Glerum et al., "Cloning and Identification of HEM14, The Yeast Gene for Mitochondrial Protoporphyrinogen Oxidase", Yeast 12: 1421-1425, 1996.

* cited by examiner

FIG. 1: Summary of enzymatic pathways in the biosynthesis of heme

FIG. 3
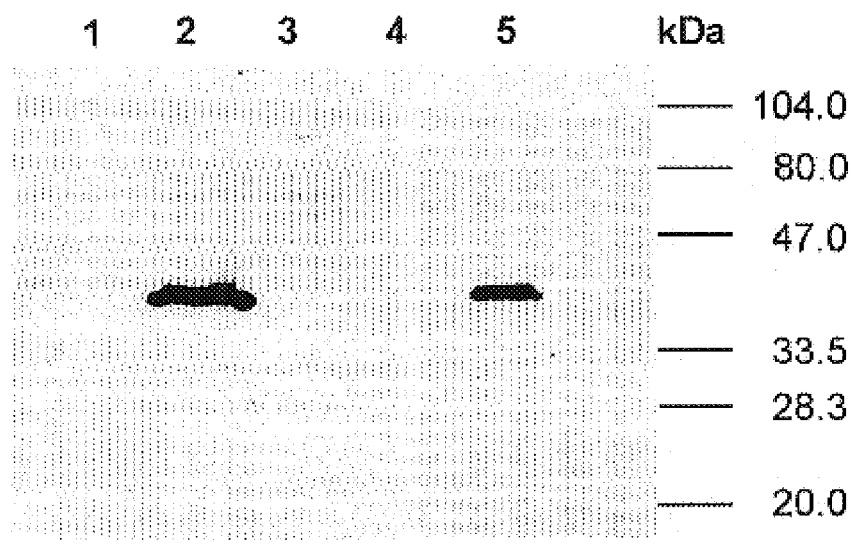
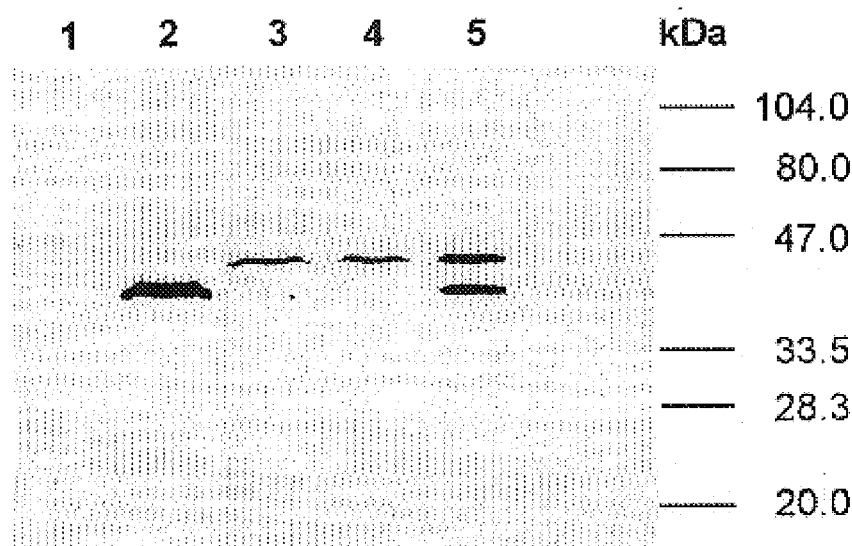

LEISHMANIA AS CARRIERS FOR THE DELIVERY OF PROTEINS AND PEPTIDES

TECHNICAL FIELD

The present invention is related to the use of trypanosomatids as biological carriers for genes of interest, and more specifically, the use of such carriers to deliver and release therapeutic or prophylactic gene products in mammalian cells.

REFERENCE TO SEQUENCE LISTING

A sequence listing is included as a part of this disclosure and all information contained therein is incorporated herein by reference.

BACKGROUND OF THE INVENTION

Proteins and peptides have the potential to be valuable prophylactic and therapeutic agents in humans and other animal subjects. However, because proteins and peptides are larger and more complex than conventional organic and inorganic drug molecules, the formulation and delivery of such agents present unique problems. In this regard, potentially beneficial protein and peptide drugs typically require the maintenance of their conformational integrity in order to be efficacious with regard to their desired biological properties against the intended targets. A protein's conformation can be altered by any of the numerous protein degradation pathways present in the body.

While there have been extensive and ongoing research efforts focused on novel ways to successfully deliver protein and peptide drugs to their intended targets, effective delivery techniques for these agents have not been perfected.

The present invention relates to the design and development of new types of biological carriers for efficient delivery of medically useful peptides and proteins. These carriers are designed for time-controllable, rapid and tissue-targeted release of the reagents. The strategies to acquire these properties are to construct the carriers from heme biosynthesis deficient trypanosome mutants (Sah et al, 2002). They are transgenically modified, making them responsive to external signals to induce accumulation of porphyrins. The porphyric state mediates cytolysis of the mutant "carriers," thereby releasing pharmaceutically useful proteins overexpressed by them via pre-transfection with relevant genes of interest. The inherent tissue-specific infection of trypanosomes is exploited for targeting.

Porphyrins are metabolic intermediates in the biosynthesis pathway of heme (Sassa and Nagai 1996). Heme is an indispensable component required for respiration to produce energy in all aerobic organisms, including humans. All porphyrin intermediates formed in this pathway, i.e. uroporphrynogen I, uroporphyrinogen III, coproporphyrinogen III, protoporphyrinogen IX, and protoporphyrin IX are also inherently cytotoxic, especially on exposure to UV irradiation. This results in the generation of free radicals due to photosensitivity of porphyrins. Abnormal accumulation of porphyrins has been reported to result from a dysfunctional heme biosynthesis pathway, leading to human diseases known as "porphyria." (Sassa 2000). Porphyric individuals suffer from photophobia, tissue necrosis, organ failure and other related systemic disorders. There are different forms of human porphyria, caused by the accumulation of different porphyrin species, resulting from genetic defects of different porphyrin metabolizing enzyme as well as their inhibition by environmental poisons, such as lead.

Application of porphyrins or their precursor, delta-aminolevulinate (ALA) alone is considered to have therapeutic potentials against microbial infection and tumors, especially when this is followed by UV irradiation (Wainwright 1998; Friesen et al. 2002). These procedures have been shown to kill certain pathogenic microorganisms and, more recently, tumor cells in "photodynamic therapy." In the latter cases, porphyrins are either administered exogenously or induced endogenously within the tumor cells using ALA, the product of ALA-synthase (ALAS)—the first of the eight enzymes in the heme biosynthesis pathway of mammals. The porphyric state generated by either way is non-targeted and transient, and the level of porphyrin accumulation is relatively low. This is due to the substrate "flow-through" and/or feedback and allosteric inhibition in the presence of a complete heme biosynthesis pathway in all aerobic organisms.

Numerous biological carriers of microbial origin have been constructed to deliver drugs and vaccines for potential medical applications (Mollenkopf et al. 2001; Edgeworth et al 2002). Induction of porphyria in microbial carriers for self-destruction presents itself as a potential strategy to achieve simultaneous elimination of the carrier and effective drug release. The feasibility of this strategy is significantly enhanced by using appropriate microorganisms as the carriers with the following inherent and/or genetically modifiable properties: (1) high producer of porphyrins in response to external signals to develop porphyria for time-controllable and rapid cylolysis; (2) mammalian cell, tissue or organ affinity for site-specific "homing" delivery; and (3) ease of in vitro cultivation and transfection of these microbial carriers with available plasmids or other vectors to express foreign genes. The microorganisms with these properties include trypanosomatid protozoa, such as *Leishmania* spp.

The present invention exploits the virtual absence of heme biosynthesis pathway in trypanosomes to identify or construct their genetic mutants for time-controllable induction of an intense and sustained porphyric state, making it possible to consider their use for targeted release of pharmaceutically important peptides and/or proteins. This is the unique aspect of the present invention.

There has been no similar concept and methodology developed previously with this group of organisms for such applications. The closest materials generated previously are suicidal mutants of *Leishmania*, but they were constructed not with genes in the heme pathway, but by negative selections for virulence gene knockouts (Titus et al. 1995; Alexander et al. 1998; Gourley et al. 2001; Papadopoulou et al. 2002) or by reverse genetics using widely publicized schemes, e.g., transfection with thymidine kinase gene for responsiveness to ganciclovir as the trigger (LeBowitz et al. 1992). These suicidal mutants also incorporate no time-controllable elements, as designed in the present invention.

Other materials peripherally related to the constructs of the present invention are knockout mutants of individual genes encoding porphyrin metabolizing enzymes in single cell organisms, e.g., algae, yeasts (Kurlandzka et al. 1991; Glerum et al. 1996) and *Chlamydomonas* (Wang et al. 1975). These mutants have been used for isolation of specific porphyrin species, but have not been considered for use as drug delivery vehicles. Creation of an additional mutation in these engineered or natural mutants for an ALAS negative phenotype is theoretically possible to render them conditional to exogenous ALA for developing porphyria. Such mutant living organisms, are not mammalian cell-, tissue- or organ-specific. Remotely relevant are single experimental steps used in photodynamic therapy of tumors, i.e., ALA induction of these cells to develop a transient porphyric state (Abels et al. 1997; Gibson et. At 1999) and direct administration of porphyrins (Afonso et al. 1990) or other chromogens followed by UV irradiation (Spikes and Bommer 1993) or laser phototherapy (Castro et al. 1996). The aim of photodynamic therapy in these schemes is to use porphyrins for treatment, but not drug delivery as is intended in the present invention.

SUMMARY OF THE INVENTION

The present invention is directed toward the use of trypanosomatid protozoa for the delivery and subsequent release of gene products of interest within mammalian cells.

The present invention provides systems and methods for delivering protein or peptide agents into a target mammalian cell. The delivery system comprises a biological carrier comprising a trypanosomatid protozoan selected or engineered to infect the target mammalian cell. The trypanosomatid is responsive to an external signal to develop porphyria and is transgenically modified to include one or more genes expressing the desired proteins or peptides in the carrier. The carrier is introduced into the mammalian cell. The external signal is then initiated to induce porphyria in the carrier, which lyses the carrier and releases the expressed proteins or peptides within the carrier into the mammalian cell.

In a preferred embodiment, the biological carrier for the proteins or peptides comprises a trypanosomatid mutant that is selected or engineered to have a phenotype that is δ-aminolevulinate synthase-negative, δ-aminolevulinate dehydratase-positive, porphobilinogen deaminase-positive, and negative for at least one heme biosynthetic pathway enzyme downstream of porphobilinogen deaminase, including uroporphyrinogen cosynthase, uroporphrinogen decarboxylase, coproporhyrinogen oxidase, protopophyrinogen oxidase and ferrochelatase. The trypanosomatid mutant can be naturally occurring or can be genetically engineered. The external signal to induce porpohyria in the carrier is exogenous δ-aminolevulinate. In an embodiment, the lysis of the carrier is spontaneous lysis as a result of excessive accumulation of one or more intermediate metabolites in the heme biosynthetic pathway. In another embodiment, lysis of the carrier can be induced by exposure of the carrier to UV irradiation.

In an embodiment, the trypanosomatid is a *Leishmania* sp., which can include guinea pig *Leishmania enriettii*, rodent *Leishmania turinica* and reptilian *Leishmania torentolae*, and avirulent strains of pathogenic *Leishmania* spp., which are either laboratory-derived or genetically engineered by the strategies of molecular attenuation of virulence described.

In a preferred embodiment, the carrier is a non-pathogenic trypanosomatid protozoa, such as members in the genera of Crithidia, Blastocrithidia, Herpetomonas, Phytomonas, Leptomonas, *Trypanosoma* and other non-pathogenic lower trypanosomatid protozoa.

In an embodiment, the target for the carrier is the mammalian macrophage. Other targets can include polymorphonuclear phagocytes, fibroblasts and dendritic cells or any other cells susceptible to infection by genetically engineered *Leishmania* or other trypanosomatid protozoa with ligands specific to the targeted cells.

In an embodiment, genes of interest can be introduced into the carrier by incorporation into the chromosomal composition of the carrier. In another embodiment, genes can be introduced via standard plasmid vector techniques, or other techniques known in the art. In yet another embodiment, the gene of interest intended for introduction into the carrier can be one that serves any desired purpose, but preferably includes gene that expresses gene products that are therapeutic, prophylactic, and/or pharmacologically active. In still yet another embodiment, the gene of interest can code for a product that will ultimately operate antigenically as a vaccine.

The present invention further provides methods of treating a mammal by delivering a protein or peptide to the mammal via the biological carrier described above.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a summary of the enzymatic pathways for the biosynthesis of heme.

FIG. 2 is an example of constructs of mammalian genes encoding porphobilinogen deaminase (PBGD) and δ-aminolevulinate dehydratase (ALAD) in p6.5 and pX vectors specific for transfection of *Leishmania*, respectively;

FIG. 3 shows Western blot analysis of *Leishmania amazonensis* transfectants expressing δ-aminolevulinate dehydratase and porphobilinogen deaminase;

FIG. 4 shows a thin layer chromatogram showing uroporphyrin I in porphyric *Leishmania amazonensis* and that released from these cells;

FIG. 5 shows the cellular localization of porphyrin in porphyric *Leishmania amazonensis* and ALA dose-dependent release of porphyrin from these cells FIG. 6 shows the growth and porphyrin production of *Leishmania* doubly transfected with alad and pbgd in the presence of increasing ALA concentrations;

FIG. 7 shows cytolysis of J774A1 monocytic tumor cells exposed to porphyric *Leishmania*; and FIG. 8 shows selective lysis of intra-macrophage *Leishmania* rendered porphyric with ALA followed by UV irradiation to release expressed episomal gene products of neomycin phosphotransferase.

DETAILED DESCRIPTION OF THE INVENTION

While this invention is susceptible to embodiments in many different forms, it is shown in the drawings and will herein be described in detail a preferred embodiment of the invention with the understanding that the present disclosure is to be considered as an exemplification of the principles of the invention and is not intended to limit the broad aspect of the invention to the embodiments illustrated.

The present invention is directed toward new biological carriers of prophylactic and/or therapeutic proteins and peptides. The present invention provides systems and methods for delivering proteins or peptides into a target mammalian cell. The delivery system comprises a biological carrier comprising a trypanosomatid selected or engineered to infect the target mammalian cell. The trypanosomatid is responsive to an external signal to develop porphyria and is transgenically modified to include one or more additional genes expressing the proteins or peptide in the carrier. The carrier is then introduced into the mammalian cell and the external signal is initiated to induce porphyria in the carrier to release the expressed proteins or peptides within the carrier into the mammalian cell.

Trypanosome parasites are especially amenable to transgenic modifications to "condition" them for porphyrin-mediated self-destruction by exploiting their extensive deficiency in the heme biosynthesis pathway. The natural site-specific infection of these parasites offers the added advantage of cell-, tissue- or organ-targeting. The virtual absence of all enzymes in their heme biosynthetic pathway makes it feasible to consider genetic manipulations of these organisms to develop porphyria conditional on the presence of ALA, thereby rendering it time-controllable. ALA is an ideal chemical signal for this, since it is an inexpensive, non-toxic, water-soluble, naturally occurring compound readily transported by cells and already in clinical use (Peng et al. 1997; Bissonnette et. al 2002). The porphyric conditions of trypanosomes are expected to make such mutants cytostatic or cytolytic. It is further contemplated that UV irradiation of the porphyric mutants hastens their rapid destruction via free-radical mediated cytolysis to release the products of interest.

The construction of effective mutants with the above-mentioned properties thus requires a combination of experimental procedures designed to: (1) achieve targeted delivery by using different species of parasites or their relevant molecules, which have naturally evolved the ability to infect specific cells, tissues or organs of their hosts, including humans; (2) significantly increase the levels of their porphyria by using natural or engineered mutations, i.e., add-on, induced or spontaneous genetic blocking of individual porphyrin metabolizing enzymes in heme biosynthesis (for accumulation of different porphyrin species); (3) render them totally dependent on ALA induction from aporphyria to porphyria, i.e., ALAS-negative phenotypes selected via genetic knockout or using spontaneous mutations with the loss of this gene function; and (4) rely on porphyria-mediated cytostasis/cytolysis for slow release, and with UV-irradiation for rapid release of desired drugs carried by the mutants, and simultaneously destruction of the latter as carriers.

The use of these porphyric mutants as delivery vehicles requires additional transfection with genes encoding the desired protein drugs/antigens. Such expression vectors (LeBowitz et al. 1990;. see Tetaud et al. 2002) are already available with different selectable markers for these organisms. These genetically engineered constructs are useful to serve as a universal and time-controllable delivery capsule to improve prophylaxis and therapy of cell-, tissue- or organ-specific diseases.

Trypanosomatids Mutants as Bioligical Carriers

Trypanosomatid protozoa are among the rare example of aerobic organisms, which depends on oxidative phosphorylation, but are defective in the synthesis of heme required for electron transport respiratory complexes. This peculiar defect in tetrapyrrole biosynthesis is manifested as a nutritional requirement for hemin by these organisms in chemically defined medium. In nature, these parasitic protozoa must acquire protoporphyrin 1× or heme exogenously from their hosts as a nutritional factor (see Sah et. al. 2002). Exceptional are several entomophilic non-pathogenic Crithidia species, which harbour Proteobacteria as endosymbionts presumably to help them complete the heme biosynthetic pathway, thereby sparing their nutritional requirement for hemin as an essential growth factor (see Du et al. 1994).

Earlier biochemical studies of trypanosomatid protozoa have shown that they are deficient in heme biosynthesis. This was examined according to the following conventional heme synthesis pathway as shown in FIG. 1: glycine+ succinyl-CoA or 4, 5 dioxovalerate+alanine→δ-aminolevulinate (ALA)→porphobilinogen (PBG)→hydroxymethylbilane [by-product=uroporphyrinogen I (URO)]→ uroporphyrinogen III→coproporphyrinogen III→ protoporphyrinogen IX→protoporphyrin IX→heme. FIG. 1 also lists the eight mammalian enzymes, which are known to catalyze this pathway (Sassa 2000). Their activities are often undetectable or negligible in trypanosomatid protozoa (see Sah et. al 2002). Reported elsewhere in these organisms were the negligible activities of ALA-synthase/dioxovalerate transaminase and intact ferrochelatase—the first and the last enzymes of the pathway normally present in mitochondria. Even less or completely absent are activities of the second and the third enzymes, i.e., δ-aminolevulinate dehydratase (ALAD) and porphobilinogen deaminase (PBGD). The pathway thus appears to be incomplete in this group of organisms. Endosymbionts are thought to complement this incomplete pathway in very few Crithidia spp. by supplying the missing enzymes.

Because the overwhelming majority of wildtype trypanosomatids typically lack various enzymes associated with the heme synthesis pathway, these protozoa have the potential to be manipulated in such a way that porphyrin intermediates can accumulate at very high levels. A variety of schemes can be envisioned to accomplish this end, and thus the given scheme employed will depend on the preference of the practitioner of the present invention.

In a preferred embodiment of the present invention, the trypanosomatid employed is one that displays the following characteristics: (1) it has an ALAS-negative phenotype (See FIG. 1, Enzyme No. 1), (2) it has an ALAD-positive phenotype (See FIG. 1, Enzyme No. 2), (3) it has a PBGD-positive phenotype (See FIG. 1, Enzyme No. 3), and (4) it lacks at least one of the remaining five enzymes of the heme catalytic pathway (See FIG. 1, Enzyme Nos. 4-8). Pursuant to this embodiment, the above conditions are necessary for the accumulation of porphyrin intermediates.

The above scheme is premised on the fact that an exogenous ALA source will be used as a signal to induce a porphyric state. In this regard, due to the lack of the ALAS enzyme, the organism cannot independently produce ALA. The lack of ALA results in the absence of a substrate for the ALAD enzyme. The absence of endogenously-produced ALA therefore results in the subsequent absence of production of substrates that are involved in the enzymatic processes downstream from ALAS. Therefore, when ALA is neither endogenously produced nor available in the immediate environment, porphyrin intermediates cannot be produced and thus cannot accumulate in these protozoa.

As noted above, while the trypanosomatid protozoa must be deficient in the ALAS enzyme, the protozoa must possess the ALAD enzyme and the PBGD enzyme. If these two enzymes are not present, the exogenously-administered ALA cannot be catalyzed to produce the subsequent products of porphyrin intermediates. When both enzymes are present, ALAD converts ALA to porphobilinogen, which is converted by PBGD into hydroxymethylbilanes that spontaneously form non-enzymatically uroporphrynogen I. In this regard, uroporphrynogen I is the first of the five porphyrinogen intermediates in the heme biosynthetic pathway. As seen in FIG. 1, the other four subsequent porphyrin intermediates are uroporphyrinogen III, coproporphyrinogen III, protoporphryrinogen IX and protoporphyrin IX. All porphyrinogens are present in cells under reduced conditions and are converted spontaneously into porphyrins in the presence of oxygen.

Assuming the presence of ALAD and PBGD, when ALA is exogenously supplied to the protozoa, at least one porphyrinogen intermediate will be produced, i.e., uroporphyrinogen I. However, if all additional enzymes (downstream of PBGD) of the heme synthetic pathway are present in a given organism, then the overall reaction pathway will progress efficiently and will ultimately result in the production of heme. In this case, the accumulation of porphyrin intermediates will not occur. It is therefore necessary that the organism lack at least one enzyme downstream of PBGD.

This most preferred embodiment of the present invention again employs mutants that (1) lack the ALAS enzyme, (2) possess the ALAD enzyme, (3) possess the PBGD enzyme, and (4) lack at least one heme synthetic pathway enzyme downstream of the PBGD enzyme. It must be stressed, however, that the present invention is not limited to the use of mutants that possess the above-four requirements. In this regard, the present invention is intended to encompass any scheme, in which a mutant trypanosomatid (genetically engineered or naturally occurring) is such that porphyrin intermediates can accumulate and subsequently cause autocytolysis of these protozoa due to the introduction of an external signal. Many such schemes can be envisioned. The guiding principles of such schemes, however, are that the phenotype of the mutant must be such that (1) the accumulation of porphyrinogen intermediates is induced by an external signal, and (2) once the production of porphyrinogen intermediates is initiated, accumulation of porphyrinogen intermediates occurs because at least one enzyme is lacking that would otherwise enable the porphyrinogen intermediates to ultimately be catalyzed for the formation of heme. This final product of the complete pathway is not photosensitive to UV irradiation for the generation of free radicals and is susceptible to disposal by heme degradation pathway.

Wildtype trypanosomatids typically will not be suited for practicing the present invention. This is because wildtype trypanosomatid typically do not posses the ALAD enzyme. Trypanosomatid protozoa useful for the present invention can be either naturally occurring mutants or genetically-engineered mutants.

Methods for screening naturally-occurring genetic and phenotypic mutants are well-known in the art.

Methods for engineering mutants suitable for practicing the present invention are also well-known in the art. In this regard, methods for such engineering include, but are not limited to "knock-out," "knock-in," and "blocking" methods at the gene level as well as anti-sense and RNAi inhibition of mRNAs at the translational level.

Porphyric mutants can be screened and/or constructed from non-pathogenic parasite species, e.g., guinea pig *Leishmania enriettii*, rodent *Leishmania turinica* and reptilian *Leishmania torentolae*; avirulent strains of pathogenic *Leishmania* spp.; and other non-pathogenic trypanosomatids and related protozoa, e.g., Crithidia, Blastocrithidia, Herpetomonas, Phytomonas and *Leptomonas*. The use of these cells will alleviate the potential concern that the residual parasites, which survive the infection or UV irradiation, may cause leishmaniasis/parasitic diseases in the recipients. Avirulent L. major, for example, is a suitable choice, as it causes mild cutaneous infection, which becomes resolved spontaneously. Most of these organisms and their transfectants can be readily grown in simple available culture media and also in chemically defined media in liters for industrial scales.

Alternatively, other species of parasites can be genetically engineered directly to become porphyric and used as delivery vehicles for targeting to other tissues by the same approaches with some modifications.

Transfection of *Leishmania* and other trypanosomatid protozoa with genes encoding additional porphyrin metabolizing enzymes will be useful to produce other types of prophyria with different species of porphyrins, e.g., coproporphyrins and protoprophyrin IX. Their different properties, e.g., hydrophobicity, will have relevance to cytoxicity and targeted delivery of such mutant constructs.

The target for the carrier depends on the trypanosomatid selected and the specific host cells it infects. In a preferred embodiment, the target is the mammalian macrophage. Other targets can include polymorphonulear phagocytes, fibroblasts and dendritic cells. *Leishmania*, for example, is known to specifically infect macrophages and dendritic cells. *Leishmania* cell- or tissue-specificity can be further genetically altered by incorporating ligand molecules from other cell-, tissue- or organ-specific parasites. Constructs so engineered are expected to "home-in" toward specific cells and tissues other than macrophages.

The biological carrier can be used to deliver the protein or peptide to a mammal to treat the mammal by administering the carrier encoding the protein or peptide of interest to the mammal. Administration of the carrier to a subject can be achieved by techniques that are well-known in the art. By way of example and not limitation, such administration techniques can include topical application, intramuscular injection, subcutaneous injection, intravenous administration and other parenteral, enteral, dermal routes of administration, inhalation, transbucal, and nasal administration.

Lysis of Mutant Trypanosomatids

As noted above, an aim of the present invention is to introduce genes of interest into the mutant for eventual release of desirable gene products as a result of lysis of the porphyric mutant. Lysis can be induced by administration of exogenous ALA, for example. In this regard, ALA provides a substrate for the catalytic activity of the ALAD enzyme. Depending on the nature and extent of the downstream enzymes present in the heme biosynthetic pathway of the mutant, one or more porphyrin intermediates will accumulate, causing the mutant to eventually become porphyric. A natural consequence of sufficiently excessive porphyria will be lysis of the mutant. The administration of ALA to induce a state of porphyria therefore provides a time-controllable mechanism to provide release of the expressed peptide or protein of interest.

The external signal used to initiate porphyrin accumulation will depend on the overall scheme associated with the heme biosynthetic pathway enzymes present in the mutant. The external signal will therefore depend on the preferences of the practitioner of the present invention.

Administration of the external signal to initiate accumulation of porphyrin intermediates (e.g., administration of ALA) can be achieved by techniques that are well-known in the art. By way of example and not limitation, such administration techniques can include topical application, intramuscular injection, subcutaneous injection, intravenous administration and other parenteral, enteral, dermal routes of administration, inhalation, transbucal, and nasal administration.

Pursuant to the present invention, exposure of porphyric *Leishmania* to UW irradiation can result in a more rapid release of the peptide or protein sought to be delivered. In this regard, it is thought that exposure to UV irradiation of porphyric mutants hastens their rapid destruction via free-radical mediated cytolysis. To accomplish this end, the subject that carries the mutant must be exposed to UV irradiation. The optimal conditions associated with the UV irradiation exposure (e.g., wavelengths, duration, location, and intensity of the exposure) will vary depending on the preferences of the practitioner of the present invention and the target mammalian cells.

Protein/peptide Gene Products Expressed in the Mutant

Genes encoding various peptides and proteins of potential prophylactic and/or therapeutic interest can be introduced into the mutant for expression and eventual release as a result of porphyria-related lysis of the mutant. Techniques for transfection of *Leishmania* with such genes are well known in the art. By way of example and not limitation, foreign genes of interest can be introduced into the chromosomal genome of the mutant, or they can be introduced by using well-known plasmid vector techniques. Examples of gene expression systems in these organisms are disclosed in International Patent Applications WO 02/44355 and WO 01/32896.

Other desirable genes can be introduced into the mutant for expression and ultimate release due to porphyria-related lysis. The gene selected for introduction into the mutant will vary depending on the preferences of the practitioner of the present invention.

Although the porphyric trypanosomatids such as *Leishmania* can be used to deliver peptide drugs for lysosomal activation, they are considered especially suitable for vaccines because they exclusively infect macrophages and dendritic cells—the very cells which process and present antigenic epitopes to the mammalian immune systems for eliciting effective immunity. The vaccine-expressing *Leishmania* constructs are expected to end up in the phagolysosomes of these antigen-presenting cells when delivered to animals as do the wildtype *Leishmania*. Subsequent administration of ALA lyses the intralysosomal *Leishmania* constructs, thereby concentrating "vaccines" for release and exposure to this antigen processing site for effective presentation. *Leishmania* has been reported to effectively deliver ovalbumin to macrophages for presentation of its antigenic epitopes to CD+ T-cells (Kay et. al 1993). Time-controllable release of this and other antigens has not been incorporated into the previous schemes, but it is expected to heighten the level of the immune response. This is achievable through the use of porphyric *Leishmania*. In addition, cytolysis of the porphyric "carrier" *Leishmania* with or without UV irradiation minimizes the risk of leishmaniasis, especially when non-pathogenic or avirulent species and strains are used. Both human and veterinary applications of the "vaccine" delivery by porphyric *Leishmania* can be considered under the same principles.

By way of further example and not limitation, examples of the present invention will now be given.

EXAMPLE 1

Cell Cultures

Wildtype *Leishmania amazonensis* (LV78) promastigotes (clone 12-1) were grown at 25° C. in Medium199 Hepes-buffered to pH 7.4 and supplemented with 10% heat-inactivated fetal bovine serum (HIFBS). Transfectants were grown under similar conditions with different concentrations of selective pressure, i.e., G418 and/or tunicamycin. Cells were also adapted to grow in a chemically defined medium. To initiate such cultures, cells were washed twice with the defined medium by centrifugation at 3,500 g for seeding at 2-5×10$^6$ cells/ml. Cells were counted using a hemacytometer. Macrophages (J774A1) were grown in RPMI 1640 supplemented with 10% or 20% heat-inactivated FBS at 35° C. Cultures of all cells rendered porphyric were kept in the dark to avoid cytolysis due to photosensitivity.

EXAMPLE 2

Cloning of the cDNAs

Figure 2:
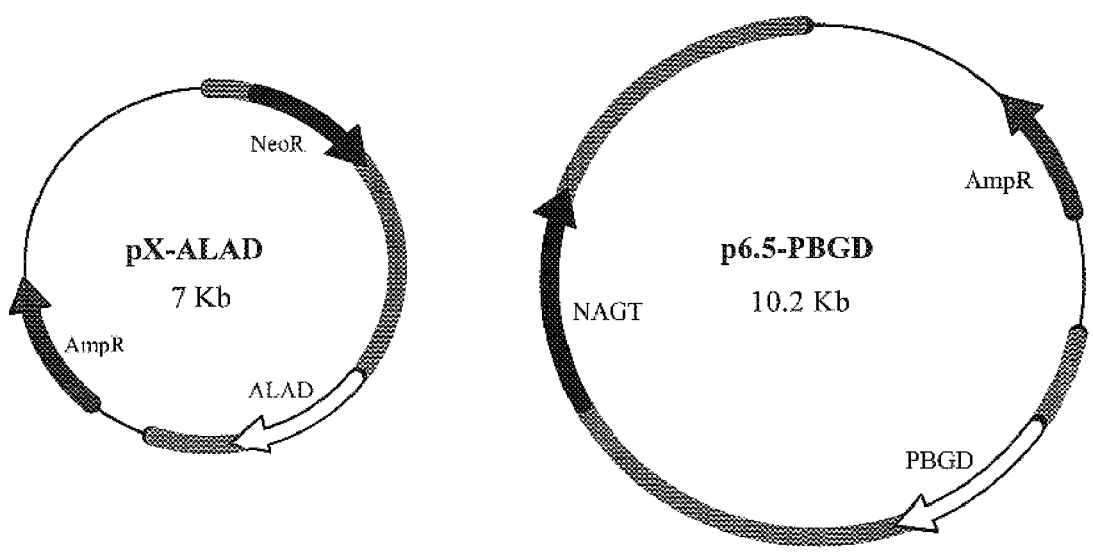

FIG. 2, which illustrates an example of an embodiment of the present invention, shows constructs of mammalian genes encoding porphobilinogen deaminase PBGD and δ-aminolevulinate dehydratase ALAD in p6.5 and pX vectors specific for transfection of *Leishmania*, respectively. Gray arrowed bars represent ampicillin resistance gene (AmpR). The thicker gray area is *Leishmania* DNA containing neomycin phosphotransferase gene (NeoR) and N-acetylglucosamine-1-phosphate transferase (NAGT) (dark arrowed bars) as selectable markers .of *Leishmania* for G418 and tunicamycin, respectively. Arrow indicates the direction of transcription.

The cDNA of rat PBGD (1038 bp) (Accession # X06827) was obtained by digesting the plasmids with BamHI. The human ALAD (993 bp) (Accession # M13928) was amplified by polymerase chain reactions (PCR) from a cDNA cloned in pGEM-T vector using a high fidelity Taq polymerase (Expand Hi Fi, Boehringer). The forward and reverse primers used were SEQ ID NO:1 (5'-TGC-CCACTGGATCCCCGCCATG-3') and SEQ ID NO:2 (5'-CACTGGGATCCATCATTCCTCC-3'). To facilitate cloning into the *Leishmania* expression vectors, the primer sequences were designed to include BamHI sites (underlined) flanking the PCR products. The amplified products of alad was first cloned in pGEM-T for expansion and then gel-purified after BamHI digestion for cloning into *Leishmania*-specific vector, pX-neo. The rat pagd was cloned into p6.5 with N-acetylglucosamine-1-phosphate transferase gene or nagt for tunicamycin-resistance. The clones with the inserts in correct orientation were identified by restriction mapping. Promastigotes were transfected with pX-alad and/or p6.5-pbgd (see FIG. 2) by electroporation as described earlier, and selected initially for resistance up to 10 µg tunicamycin/ml or 20 µg G418/ml or a combination of both. Stable transfectants emerged in 8-10 days and were subsequently passaged continuously in media with appropriate drug pressures.

EXAMPLE 3

Western Blot Analysis

Stable transfectants grown in Medium199 supplemented with heat-inactivated FBS and selected with appropriate drugs were assessed for the presence of ALAD and PBGD by Western blot analysis. Briefly, protein samples each equivalent to 20×10$^6$ cells were subjected to SDS-PAGE using MiniProtean II (BioRad) and blotted to nitrocellulose. The primary anti-PBGD and anti-ALAD antisera were generated by immunization of rabbits with purified enzymes. Both were used at 1:10$^5$ dilution. Peroxidase-conjugated goat anti-rabbit IgG (Sigma) was used as the secondary antibody. Immunoblots were subsequently developed with the ECL reagent (Amersham) and exposed to X-ray films.

Western blot analysis of various cell lysates revealed that both enzymes were undetectable in the wildtype (FIG. 3, Lane 1) and appeared as specific protein bands of the expected size (FIG. 3, Lanes 2-5) in the transfectants. Probing the blots with anti-ALAD antiserum alone revealed a single band of 36 kDa in the transfectants with pX-ALAD (Panel A, Lane 2) and those with this plasmid in combination with p6.5-PBGD (Panel A, Lane 5), but not in those with p6.5-PBGD and p6.5-PBGD +pX (Panel A, Lanes 3-4). Reprobing the same blot with anti-PBGD antisera showed that transfectants with pX-ALAD (Panel B, Lane 2), p6.5-PBGD (Lane 3) and p6.5-PBGD +pX (Lane 4) each contained single bands of the expected size, i.e,. ~36 kDa or ~42 kDa, respectively, while those with both genes (Lane 5) contained both protein bands. The results thus indicate that both genes were expressed at the protein level individually in different transfectants and simultaneously in the same one using different vectors.

EXAMPLE 4

Enzyme and Porphyrin Assays

Cells were harvested by centrifugation for five minutes at 3,500 g, resuspended in phosphate buffer saline (pH 7.4) and lysed by three cycles of freezing-thawing in dry ice/acetone bath. Cell lysates equivalent to $20\text{-}50\times10^6$ cells and to $2\text{-}5\times10^6$ cells were used for ALAD assays and PBGD assays, respectively. The activity of ALAD was assayed by monitoring absorption at 553 nm for the color salt of porphobilinogen using the modified Ehrlich reagent. PBGD activities were assayed by a microfluorometric method. Porphyrin levels were determined fluorometrically using 5 µl of cell suspensions ($=2\text{-}5\times10^6$ cells/ml) and 0.5 ml of 1 M perchloric acid/methanol (1:1, v/v). Samples were assayed for proteins using Coomassie R-250 dye-binding.

The type of porphyrins produced was determined by thin-layer chromatography (TLC) of relevant samples using porphyrin ester chromatographic marker kit as the standards (Porphyrin Products Co., Logan, Utah). Cells were grown in porphyrin-free chemically defined medium to $3\text{-}4\times10^8$ cells. Porphyrins were extracted from the cell pellets, methylated and analyzed by TLC.

Both ALAD and PBGD activities were absent in wildtype cells (not shown) and present only in transfectants with the genes of relevance (Table 1). The specific activities in pmol products/mg protein/hr fell within the range of ~2,500 to ~9,500 and ~400 to ~1,400 for ALAD and PBGD, respectively. The variations in the specific activities among different experiments seen may be accounted for by differences introduced inadvertently in the culture and selective conditions used. Clearly, both enzymes were fully functional alone or in combination in the transgenic Leishmania cells.

TABLE 1

ALAD and PBGD specific activities in Leishmania transfectants

| | ALAD activity (pmol PBG/mg protein/h) | | | PBGD activity (pmol URO/mg protein/h) | | |
|---|---|---|---|---|---|---|
| | [1]transfectants containing: | | | | | |
| Expt. No. | alad | pbgd | alad & pbgd | alad | pbgd* | alad & pbgd |
| 1 | 9528 | 0 | 8187 | 0 | 1380 | 698 |
| 2 | 9230 | 0 | 6542 | 0 | 985 | 420 |
| 3 | 2660 | 0 | 3910 | 0 | 491 | 690 |

[1]Grown to stationary phase in a defined medium and harvested for enzyme assays as described in Materials and Methods. See FIG. 1 for the plasmid constructs used for the transfection.
*Transfectants with the pX vector alone in addition to p6.5-pbgd.

Figure 4:
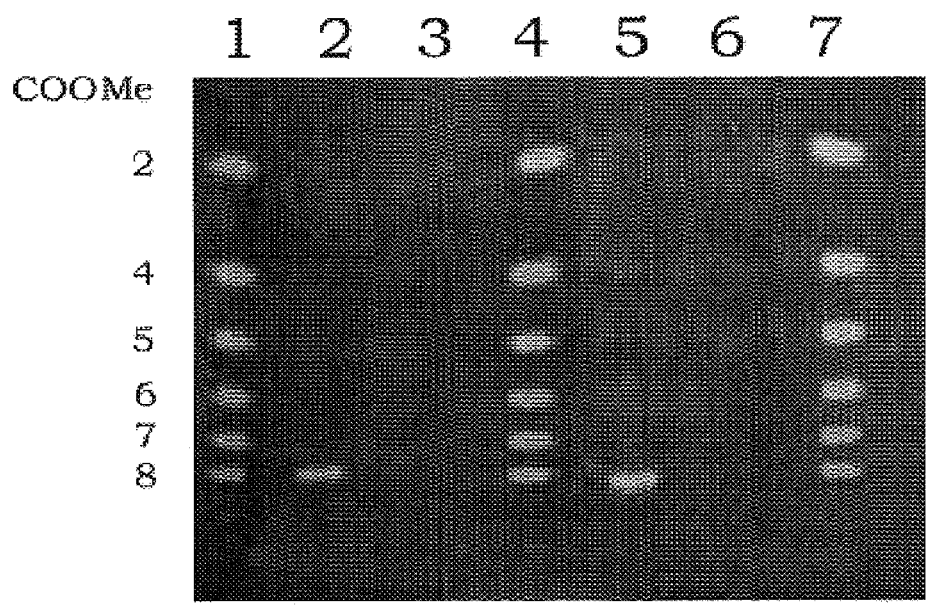
Figure 5:
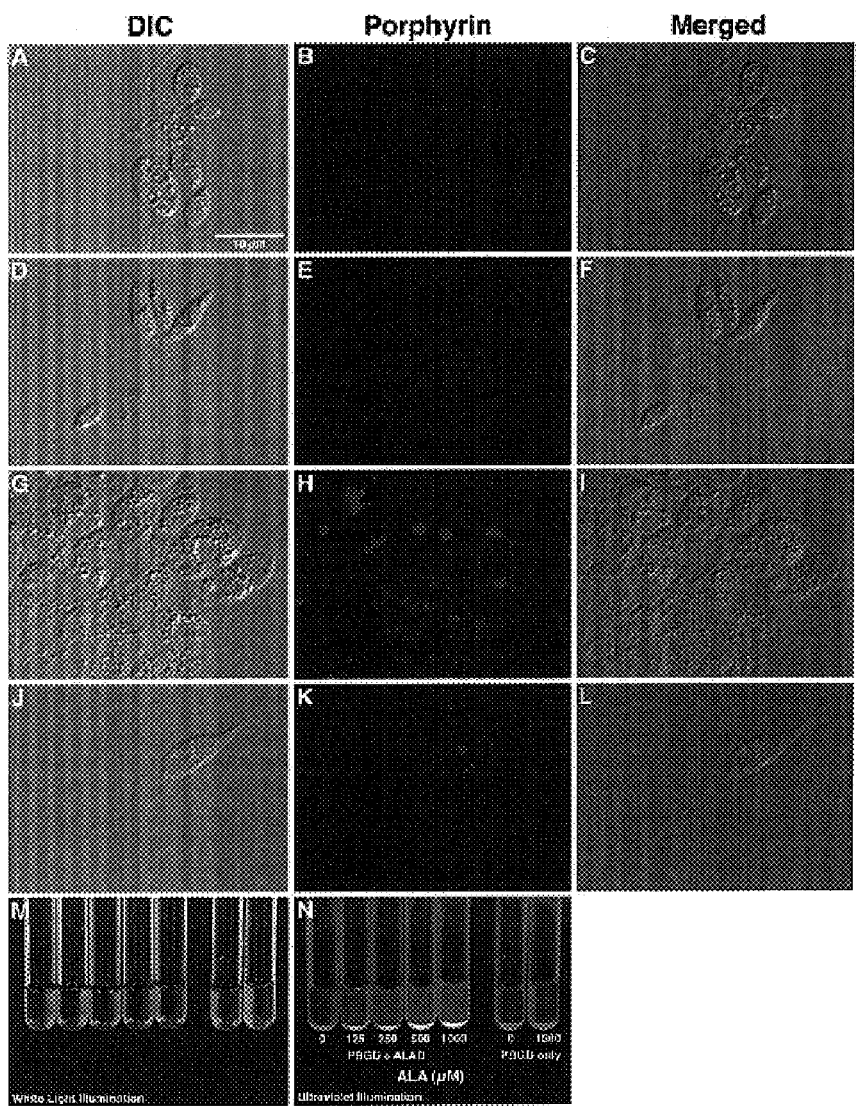

While both ALAD and PBGD were expressed and fully active in Leishmania transfected with the respective gene, the transfectants produced no detectable porphyrins (see FIG. 4, Lanes 3 and 6; FIG. 5, Panel N, 0 ALA) unless ALA was provided to those with both transgenes (FIG. 4, Lanes 2 and 5; FIG. 5, Panel N 125-1000 µM ALA). However, this porphyric Leishmania along with all other transfectants resemble non-transfected wildtype cells in that they grew continuously only in the defined medium supplemented with either hemin or protoporphyrin IX (data not shown). Deletion of the heme compound from this medium resulted in the eventual cessation of their growth in all cases after several passages. Heme biosynthesis pathway thus remained incomplete in these transgenic Leishmania, clearly due to additional enzymatic defect(s) downstream of PBGD.

Uroporphyrin I was the sole intermediate detected in porphyric Leishmania. This was originally suggested by the fluorescence emission spectra of porphyrins extracted from porphyric Leishmania observed (data not shown) and confirmed by TLC analysis of these samples (FIG. 4). TLC of porphyrins extracted by standard procedures from porphyric Leishmania and their spent medium revealed only a single UV-fluorescent species (FIG. 4, Lanes 2 and 5), which co-migrateed with uroporphyrin I octamethyl esters (Lanes 1, 4 and 7). This finding indicates that only uroporphyrin I was produced by these cells. No porphyrin bands were visible in samples prepared simultaneously from controls, e.g., transfectants with one or the other gene and their culture supernatants (FIG. 4, Lanes 3 and 6). The cells used for sample extraction were grown in porphyrin-free defined medium, eliminating the possibility that the porphyrin species detected may have derived from an exogenous source.

EXAMPLE 5

Porphyrin Fluorescence Microscopy

For all microscopic examinations of Leishmania, living cell suspension in 5-10 µl aliquots was placed on a glass slide and then covered with an 18 mm² glass coverslip. For routine examinations, the preparations were viewed under phase contrast for cellular structures in conjunction with epifluorescence for porphyrins using a filter set consisting of D405/10X (405 nm exciter), 485DCXR (485 nm dichroic) and RG610LP (610 mm emitter) (Chroma Tech Co, Brattleboro, Vt.) in a Zeiss standard microscope with super pressure mercury lamp (HBO 50 W, Osram). Images were obtained by confocal microscopy using an Olympus FluoView confocal microscope equipped with a Krypton/Argon mixed gas laser. Specimens were illuminated with the 488 mm excitation line. The specific fluorescent emission of the porphyrin was collected by a photomultiplier tube after passing through a 605 mm bandpass emission filter. Differential interference contrast (DIC) images were simultaneously collected using a transmission field detector coupled to a photomultiplier tube. Detection settings were determined using a negative control by adjusting the gain and offset settings to eliminate background. Images were collected using a 100× oil immersion objective (NA 1.40) with an electronic zoom of 3×. The confocal aperture was set to 5 mm to maximize the depth of field within the specimen. Digital image acquisition took approximately 7 seconds per frame, resulting in movement-induced blurring of the flagella in viable specimens. Images were composed in Adobe Photoshop. Only DIC images were adjusted for brightness.

The porphyrins emerged only in the double transfectants after the addition of ALA into their culture media. Porphyrin-specific signals were followed by epifluorescent microscopy and imaged by confocal fluorescent microcopy (see above for the settings used). By differential interference contrast microscopy, living cells under all conditions used appeared granulated with anterior flagella (FIG. 5, Panels A, D, G and J). Under the settings for confocal microscopy used for porphyrin, fluorescence signals emerged only in the double transfectants (FIG. 5, Panels H and K), but not in the control cells, e g., the single transfectants with PBGD alone (Panels B and E). When the two sets of images from the same preparations were merged, porphyrin fluorescent signals appeared to be diffused in the cytosol (FIG. 5, Panel I) as well as localized in cytoplasmic vacuoles (Panels I and L).

EXAMPLE 6

Accumulation and Release of Uroporphyrin

Figure 6:
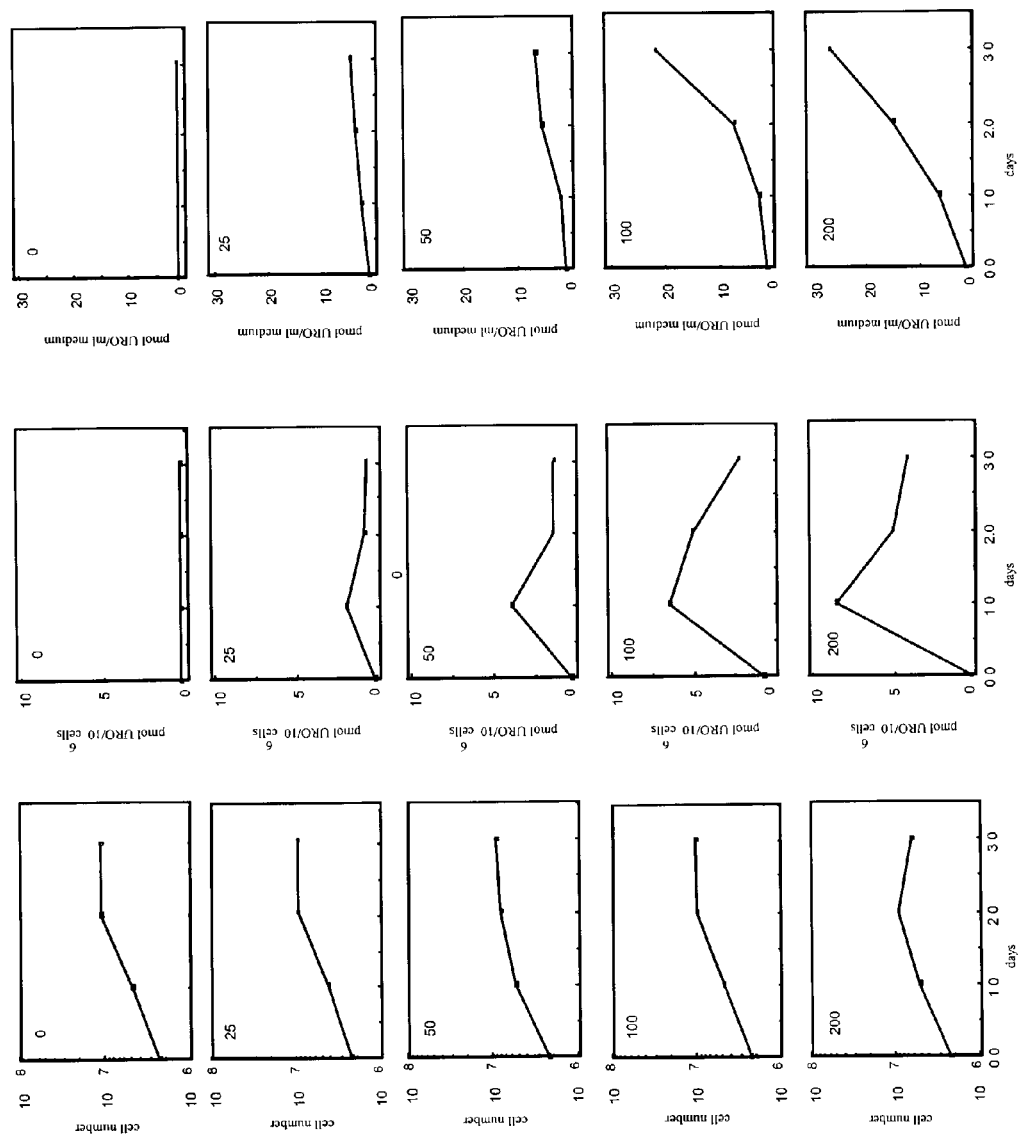

Porphyric *Leishmania* releaseed uroporphyrin I into the medium, independent of cytolysis. This was demonstrated under two different conditions to generate modest and high levels of uroporphyria. Cells were handled gently to avoid inadvertent cytolysis. The kinetics of uroporphyrin accumulation in and release from porphyric *Leishmania* was quantitatively assessed fluorometrically. Initially used were cells grown in a chemically defined medium with a modest selective pressure of 2 µg tunicamycin and 10 µg G418/ml in conjunction with increasing, but low concentrations of ALA from 0 to 200 µM (FIG. 6). Under all these conditions, cells grew from $2.5 \times 10^6$/ml to $\sim 10^7$/ml in a period of three days (FIG. 6, Left panels), except the one with the highest ALA concentration of 200 µM, in which case the cell density decreases on day 3 (FIG. 6, Bottom left panel). In the absence of ALA, porphyrin was detected neither in cells nor in their spent media throughout the period of cell growth (FIG. 6, Top middle and right panels). In the presence of ALA, the cells produced uroporphyrin in an ALA dose-dependent manner, namely an increase from ~3 to ~8 pmol uroporphyrin $10^6$ cells in the presence of 25 to 200 µM ALA during the first day (FIG. 6, Middle Panels). The cellular levels of uroporphyrin declined in these cells from day 2 to day 3, concomitant with its release also in an ALA dose-dependent manner from 5 to 28 pmol uroporphyrin/ml in the culture medium (FIG. 6, Right Panels).

In a separate set of experiments, cells were grown in Medium 199 plus heat-inactivated FBS under the optimal conditions for uroporphyria, i.e., a 10-fold increase of the selective pressure (20 µg tunicamycin and 100 µg G418/ml) and a 5- to 8-fold increase of the substrate (up to 1.0-1.6 mM ALA provided exogenously). Under these conditions, both cellular and released uroporphyrin levels were considerably enhanced (FIG. 5, Panels N 125-1000 µM ALA), the latter reaching a level as much as ~2 µM. Cytolysis was observed in <1% of these cells that did not account for the level of porphyrin release seen.

The results from both sets of the experiments indicate that uroporphyria was induced in an ALA dose-dependent fashion, which was marked by initial cellular accumulation of uroporphyrin followed by its release and accumulation in the culture medium.

EXAMPLE 7

UV Sensitivity Assays

For these experiments, transfectants with ALAD and PBGD, and those with the latter alone were grown in chemically defined medium supplemented with up to 1.6 mM ALA to generate different levels of porphyria. Cell suspensions in 24 well microtiter plates ($10^7$ promastigotes/ml/well or $5 \times 10^6$ promastigotes $+5 \times 10^5$ J774A1 macrophages/ml/well) were irradiated after infection or immediately at room temperature under a longwave UV lamp (254-366 nm multi-bands, Mineralight Lamp, Model UVSL-58, Ultraviolet Products, Inc, San Gabriel, Calif.) placed ~5 cm above the cell layers. Porphyric *Leishmania* prepared under other conditions and their spent media with different concentrations of released porphyrins were also examined for their effects on J774A1 cells. After illumination for variable time periods, cells were microscopically examined immediately. Cells of the monocytic tumor line were counted using a hemacytometer 1-2 days after irradiation. All experiments were repeated at least twice.

Porphyric *Leishmania* remained motile and thus viable under all culture and selective conditions used, except when they were subjected to UV irradiation. This sensitivity was indicated by the immediate cessation of the motility of the early porphyric cells after exposure to illumination under the setting for epifluorescent microscopy or with the long wave UV lamp. Late porphyric cells exposed to ALA two days or longer were less sensitive, while non-porphyric cells were totally insensitive to UV irradiation under these conditions, as indicated by their motility.

Figure 7:
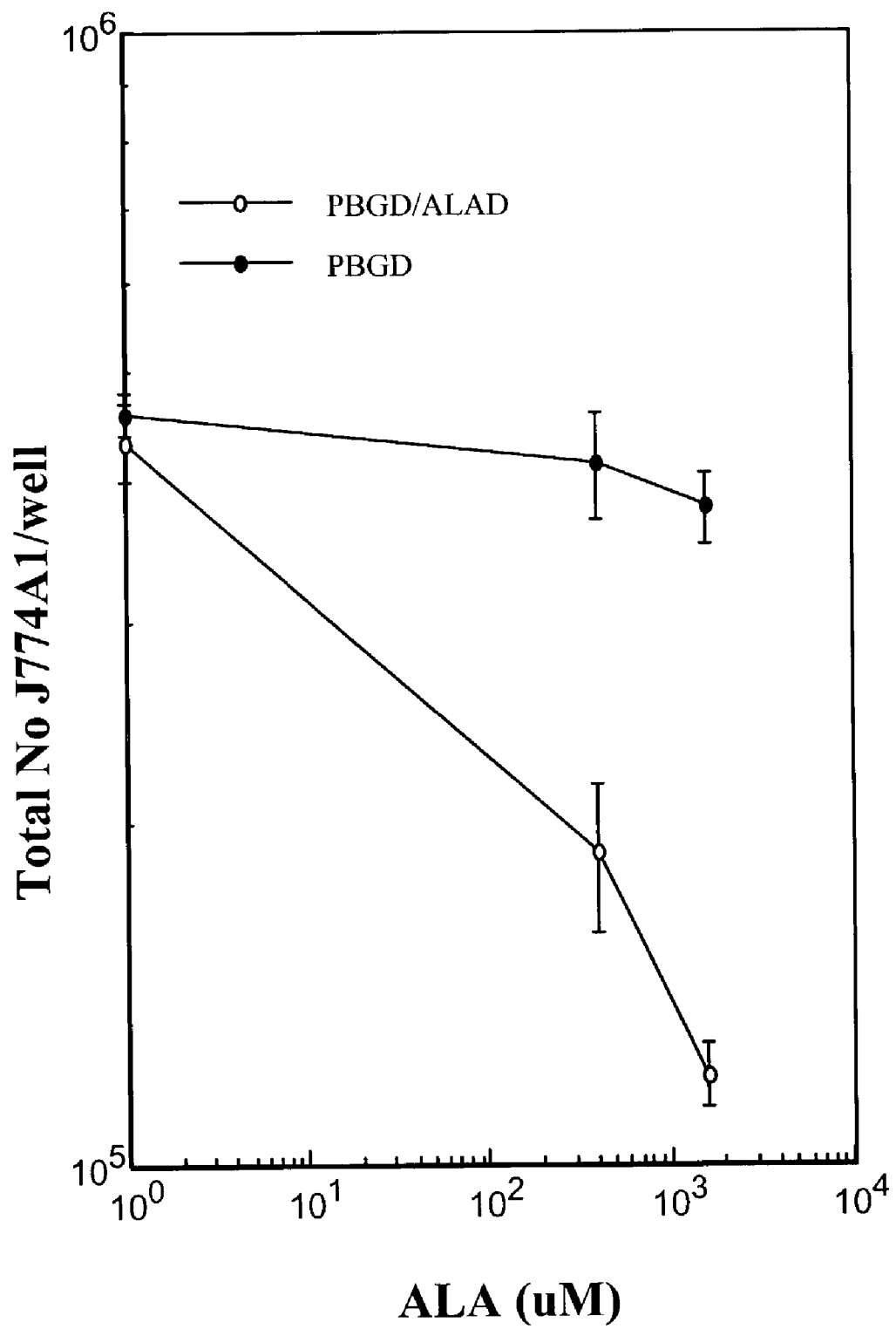

The monocytic tumor cells, J774A1 cells were also rendered sensitive to long wave UV irradiation after infection with porphyric *Leishman*. Used for these experiments were double transfectants with both ALAD and PBGD, and single transfectants with only the latter gene grown under the same conditions, uroporphyria being generated only in the former. The results (FIG. 7) showed that UV irradiation lysed only the macrophages infected with porphyric *Leishmania*; and that the cytolysis was proportional to the porphyric levels of the latter modulated by prior exposure to different ALA concentrations (FIG. 7, ALAD/PBGD). The non-porphyric *Leishmania* produced no such effect (FIG. 7, PBGD), regardless of their exposure to ALA and UV irradiation under the same conditions. There was also no cytolysis of the tumor cells when irradiated immediately after mixing them with the porphyric *Leishmania* or in the presence of their spent media containing uroprophyrin I. The results obtained from these experiments were similar to the control in FIG. 7 (not shown).

EXAMPLE 8

Expression of a Transgene Product

The experiments began with infecting macrophages of the J774 line with *Leishmania* doubly transfected with pX-alad and P6.5-pbdg. The selectable marker of the vector pX contains neo for expression of neomycin phosphotransferase (NEO), conferring G418-resistance on the transfectants. After infection for ~7 days, the culture was split into two sets, which were treated with and without 1 mM ALA overnight, respectively. As expected, UV fluorescent microscopy revealed that porphyrins were absent in the set without ALA treatment and present at high intensity in both macrophages and *Leishmania* of the other set treated with ALA. Both sets were subsequently incubated in the absence of ALA for 3 days so that porphyrins diminished in the macrophages to the background level, but remained highly elevated in the *Leishmania*. All cultures were then exposed to UV irradiation under conditions as described (Sah et al.

2002). Notably, UV irradiation under these experimental conditions used selectively lysed only the porphyric *Leishmania* inside the macrophages, but not the latter. This was in contrast to cytolysis of macrophages observed when they were infected with the double transfectants already rendered porphyric before infection (FIG. 7). The different experimental conditions used may produce very different photodynamic properties of uroporphyrin I, accounting for the differential outcomes observed. Cells processed under the current conditions were then fixed with 4% paraformaldehyde for evaluating NEO release from intracellular *Leishmania* by immunocytochemistry. This was carried out by the standard protocol using rabbit anti-NEO antiserum as the first antibody and biotinylated donkey anti-rabbit as the second antibody, both at 1:500 dilution. The reaction products were developed with streptavidin-Cy3. Cells were counter-stained with Sytox Green for nuclear fluorescence. Cell preparations were examined by confocal microscopy as described (Sah et al. 2002), except for the excitation wavelengths used, which were 488 m and 568 nm for Cy3 and Sytox Green, respectively. Images were collected from 8 profiles of 0.25 μm and merged.

Figure 8:
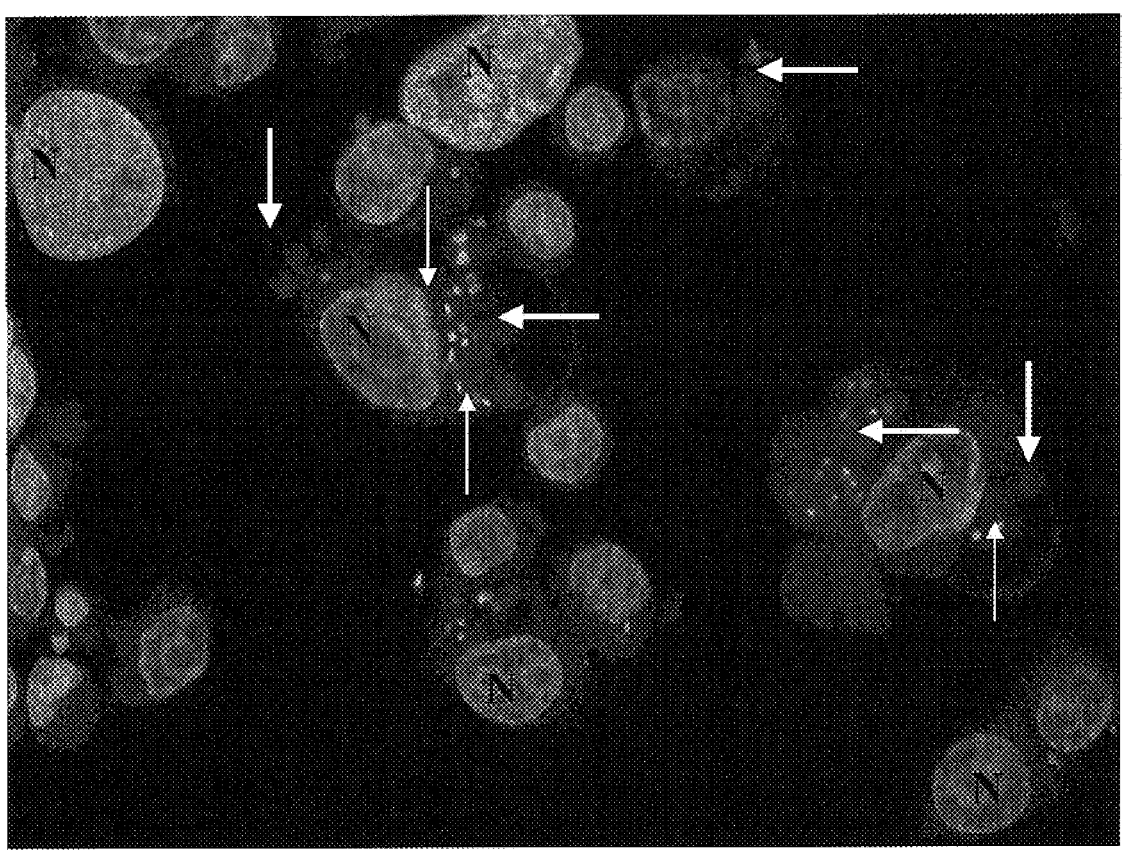

FIG. 8 shows the release of a neomycin phosphotransferase gene product (NEO) from porphyric *Leishmania* into the cytosol of infected host cells. Macrophages of J774 line were infected with *Leishmania* doubly transfected with P6.5-pbgd and pX-alad where pX vector contained a selectable marker—neo. The products of this gene, NEO, were examined for their release from porphyric *Leishmania* in the infected macrophages as an example. The infection was allowed to establish for 7 days before induction of porphyria by ALA treatment and UV irradiation, as described. Before UV irradiation, all cultures were kept for 3 more days in ALA-free conditions whereby porphyrins return to the background level in macrophages, but remained elevated in intracellular *Leishmania*. Controls were simultaneously prepared by omitting ALA treatment. All samples were fixed briefly with 4% paraformaldehyde and processed for immunocytochemistry by standard procedures using rabbit anti-NEO as the first antibody and biotinylated donkey anti-rabbit IgG as the second. Samples were developed by using streptavidin-Cy3 for reaction products of NEO and counterstained with Sytox Green for nuclei. Images were collected by confocal microscopy using appropriate wavelengths for the respective dyes used.

The Cy3 signals in orange red for NEO were seen at high intensity in infected macrophages only when treated with ALA followed by UV irradiation (see FIG. 8). These signals were absent or negligible in controls, i.e. the same materials without ALA treatment (Not shown). NEO signals appeared in the cytoplasm of some infected cells, but were not co-localized with the green fluorescence for Sytox in their nuclei (FIG. 8, N). This was consistent with the known residence of *Leishmania* in the cytoplasmic vacuoles of infected cells. There were patches of orange red fluorescent clusters in the cytoplasmic clear area, corresponding to aggregates of *Leishmania* in parasite-containing vacuoles. Each red-orange fluorescent cluster was interspersed with green-fluorescent dots, indicative of *Leishmania* DNA containing structures, i.e., parasite nuclei and kinetoplasts (=mitochondrial DNA) (FIG. 8, thin arrows). These *Leishmania* nuclei/kinetoplasts were absent in some individual structures in the orange-red cluster (FIG. 8, thick arrows), which clearly represented lysed *Leishmania* whence NEO release was expected. The released NEO was apparently insufficiently soluble or insufficiently fluorescent in the parasite-containing vacuole, which would otherwise fluoresce orange red. Although NEO in apparently lysed *Leishmania* stayed aggregated, some orange red fluorescence appeared in other part of the cytoplasm. This suggested diffusion of NEO into other cytoplasmic vacuoles and/or into the cytosolic compartment. If so, the released products from *Leishmania* would be accessible to both MHC-class I and MHC-class II pathways of antigen presentation. This is important in considering the potential use of porphyric *Leishmania* for delivering vaccines.

It is understood that, given the above description of the embodiments of the invention, various modifications may be made by one skilled in the art. Such modifications are intended to be encompassed by the claims below.

What is claimed is:

1. A biological carrier for delivering proteins or peptides to a mammalian cell selected from the group consisting of macrophages and dendritic cells, the carrier comprising:

a *Leishmania* capable of infecting the mammalian cell and having been transgenically modified to include one or more genes expressing the proteins or peptides in the carrier and being further modified to have δ-aminolevulinate dehydratase (ALAD) activity and porphobilinogen deaminase (PBGD) activity; the *Leishmania* lacks δ-aminolevulinate synthetase (ALAS) activity and lacks at least one enzyme of the heme biosynthetic pathway downstream of PBGD; and wherein the *Leishmania* is responsive to exposure to δ-aminolevulinate (ALA) to develop porphyria and lyse the carrier to release the proteins or peptides into the mammalian cell.

2. The biological carrier of claim 1, wherein the *Leishmania* is a species selected from the group consisting of: guinea pig *Leishmania enriettii*, rodent *Leishmania turinica*, and avirulent strains of pathogenic *Leishmania* spp.

3. The biological carrier of claim 1, wherein the protein or peptide is pharmacologically active.

4. The biological carrier of claim 1, wherein the protein or peptide is therapeutic.

5. The biological carrier of claim 1, wherein the protein or peptide is prophylactic.

6. The biological carrier of claim 5, wherein the prophylactic protein or peptide is antigenic.

7. The biological carrier of claim 1, wherein the gene is incorporated into a plasmid within the *Leishmania*.

8. The biological carrier of claim 1, wherein the gene is incorporated into a chromosome of the *Leishmania*.

9. A method for delivering an antigenic proteins or peptides into a mammalian cell in a mammal, the mammalian cell is selected from the group consisting of macrophages and dendritic cells, and the method comprising the steps of:

providing a biological carrier for the antigenic protein or peptide, the biological carrier comprising a *Leishmania* capable of infecting a the mammalian cell and the *Leishmania* having been modified to have δ-aminolevulinate dehydratase (ALAD) activity and porphobilinogen deaminase (PBGD) activity and further having a phenotype of:

(a) δ-aminolevulinate synthase-negative; and (b) negative for at least one heme biosynthetic pathway enzymes selected from the group consisting of uroporphyrinogen cosynthase, uroporphrinogen decarboxylase, coproporhyrinogen oxidase, protoporphyrinogen oxidase and ferrochelatase;

administering the carrier to the mammal to introduce the carrier to the mammalian cell within the mammal; and providing an effective amount of exogenous δ-aminolevulinate to induce porphyria in the carrier and lyse the carrier to release the proteins or peptides expressed in the carrier into the mammalian cell.

10. The method of claim 9, wherein the *Leishmania* is non-pathogenic.

11. The method of claim 9 further comprising exposing the carrier to U.V. light after administering the carrier to the mammal to introduce the carrier to the mammalian cell within the mammal and after exposing the carrier to exogenous δ-aminolevulinate.

12. The method of claim 9, wherein the *Leishmania* is a species selected from the group consisting of: guinea pig *Leishmania enriettii*, rodent *Leishmania turinica*, and avirulent strains of pathogenic *Leishmania* spp.

13. The method of claim 9, wherein the carrier has been transgenically modified to include a gene to express the antigenic protein or peptide.

14. The method of claim 13, wherein the gene is incorporated into a plasmid within the biological carrier.

15. The method of claim 13, wherein the gene is incorporated into a chromosome of the biological carrier.

* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Artificial
<220> FEATURE:
<223> OTHER INFORMATION: Artificial primer sequence

<400> SEQUENCE: 1
tgcccactgg atccccgcca tg                                              22

<210> SEQ ID NO 2
<211> LENGTH: 22
<212> TYPE: DNA
<213> ORGANISM: Artificial
<220> FEATURE:
<223> OTHER INFORMATION: Artificial primer sequence

<400> SEQUENCE: 2
cactgggatc catcattcct cc                                              22